(12) United States Patent
Shamie

(10) Patent No.: US 6,416,776 B1
(45) Date of Patent: Jul. 9, 2002

(54) BIOLOGICAL DISK REPLACEMENT, BONE MORPHOGENIC PROTEIN (BMP) CARRIERS, AND ANTI-ADHESION MATERIALS

(75) Inventor: Nicholas Shamie, San Francisco, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 0 days.

(21) Appl. No.: 09/505,050

(22) Filed: Feb. 16, 2000

Related U.S. Application Data
(60) Provisional application No. 60/120,486, filed on Feb. 18, 1999.

(51) Int. Cl.[7] .................................................. A61F 2/00
(52) U.S. Cl. ......................... 424/423; 514/2; 424/422; 524/17
(58) Field of Search ................................ 514/2; 524/17; 424/422, 423

(56) References Cited

U.S. PATENT DOCUMENTS

| | | | | |
|---|---|---|---|---|
| 5,945,115 A | * | 8/1999 | Dunn et al. | 424/422 |
| 6,004,573 A | * | 12/1999 | Rathi et al. | 424/426 |
| 6,005,162 A | * | 12/1999 | Constantz | 623/16 |
| 6,051,648 A | * | 4/2000 | Rhee et al. | 525/54.1 |

* cited by examiner

Primary Examiner—Samuel A. Acquah
(74) Attorney, Agent, or Firm—Fliesler Dubb Meyer & Lovejoy LLP

(57) ABSTRACT

A BMP carrier is described for use with humans and animals. The carrier includes human hair and a block copolymer of ethylene glycol and propylene glycols that can be implanted into an intervertebral disc space with the polymer in liquid form and then changing into a solid viscoelastic state. The copolymer can be a carrier for BMP. The carrier also includes processed human hair.

4 Claims, 2 Drawing Sheets

Sac comprised of for example woven hair and filled with a polymer.

BIOLOGICAL DISK REPLACEMENT, BONE MORPHOGENIC PROTEIN (BMP) CARRIERS, AND ANTI-ADHESION MATERIALS

The application claims the benefit of U.S. Provisional Application No. 60/120,486, filed Feb. 18, 1999.

FIELD OF THE INVENTION

The field of the invention relates to biological disk replacement, Bone Morphogenic Protein (BMP) carriers, and anti-adhesion materials principally for human and animal use.

BACKGROUND OF THE INVENTION

Attempts at designing an artificial lumbar disk or for that matter any artificial disk have been undertaken for decades. The potential benefit for success is evidenced by total hip and knee replacement surgery which is remarkably successful and has restored mobility for hundreds of thousands who would otherwise be crippled and in constant pain. The technology in spine surgery lags behind, where still the indicted procedure for a deteriorated joint is a fusion. A fusion is not ideal as it obliterates the joint and transfers stress to adjacent joints which in some cases may not be very healthy either. In some patients multilevel degeneration prohibits a good result from spinal fusion. Spinal fusion typically take six to twelve months to complete bony healing and currently there is still a frequent occurrence of these fusions incompletely healing and compromising the result.

A device that allows deteriorated tissue to be replaced by a construct that restores stability and function of the intervertebral disk would quickly replace the fusion procedure and might even be indicated in discectomy cases for herniated disks where there is also joint deterioration. There is currently about 400,000 back operations performed a year in the United States. The majority of such operations are disk procedures and about 20% are fusions.

Currently several disk replacement prototypes have been available or are in development. These range from hydrogel bags to complex ball bearing constructs. So far, no long term satisfactory results have been achieved in humans. Hydrogel bags look most promising, but they have only very short follow-up to date.

Examples of such disk replacement devices can be found in U.S. Pat. No. 4,772,287 (Ray), Waldemar Link prosthesis which has been in use in Europe for nine years, Depuy devices, Motech devices, Acromed devices, Sofamor Danek's line of artificial disks including Kostuik's "Spring Disc", a ball and socket type with two endplates, Hedrocel spacer, Howmedica hydrogel-based nucleus replacement, and Aesculup/JBS "prodisc" of cobalt chrome and polyethylene.

The current design requires that they be placed posteriorly (from the back) which requires significantly hazardous surgery. A disk replacement that could be delivered endoscopically and that was completely biocompatible is ideal.

The normal intervertebral disk consists of a highly hydrophilic (soaks up water) mucopolysccharide central nucleus and a tough fibrocartiliginous outer ring forming a disk-like shape in between each two vertebra. It is an amazingly efficient shock absorber, transferring compressive loads on its center to tensile (stretch) loads on its outer wall. It is analogous to a golf ball with its multilayered rubber band outer portion and a contained liquid center. With age the center chemical substance of the human disk deteriorates and losses its ability to soak up and hold onto water. This results in the nucleus gradually changing from its original gelatinous nature to one similar to crab meat. The outer wall deteriorates also and hence the beginning of the deterioration of the disk which results in symptoms in 80% of the population.

Additionally in conjunction with the replacement of disk and in other types of surgery there can be a need to induce bone growth. This is observed with vertebral type fusion devices which can be packed with bone and/or other materials which may be mixed with bone growth inducing substances.

Further with respect to surgeries directed to disk replacement and other types of surgery scaring may be a problem. Accordingly there is a need to provide anti-adhesion materials to be used in conjunction with surgeries in order to prevent adhesions.

SUMMARY OF THE INVENTION

The invention discloses novel biological disk replacement, BMP carriers, and anti-adhesion materials.

BRIEF DESCRIPTION OF THE FIGURES

FIG. 1 is attached.

FIG. 2 is attached.

DETAILED DESCRIPTION OF THE PREFERRED EMBODIMENT

Figure 1:
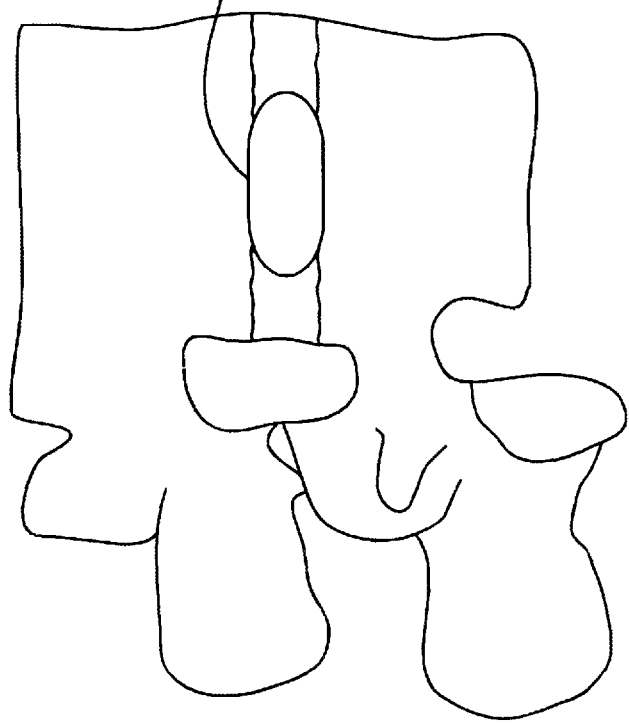
FIG. 1 is a representation of an embodiment of the first artificial disk structure of the invention with a polymer retained in a sack.

First Artificial Disk Structure:

For this embodiment (FIG. 1), a state-temperature dependent polymer can be injected as a liquid into the diseased intervertebral disk, and then can undergo a change to a solid viscoelastic state at body temperature, which can have similar properties as the normal intervertebral disk. The polymer can include, by way example, any one of the following polymers. These polymers include Poloxamer 407 and other Poloxamers, polymer combinations, and polypropylene. These polymers can be acquired under the trade names Poloxamer 407, Plannemic-Acid F127, from the following company: Sigma Aldrich. An outer covering to contain the artificial disk, which covering has sufficient tensile strength, will be necessary to maintain the disk height and prevent compression on the centrally injected polymer. Accordingly, a woven outer sack can be used to reproduce the normal disks function. This sack would need to be biocompatible to facilitate ingrowth of normal fibrous or fibrocartiliginous tissue, anchoring and melding the artificial disk with remnants of living disk tissue and/or the vertebral bone. Possible candidates for this outer sheath are various polymer compounds, and the recipients own hair processed to form a tightly woven fabric. The proteins in recipient's hair will not be subject to rejection phenomena and thus, be readily accepted by the recipient's immune system, a crucial factor for ingrowth to occur. Polymer materials which could be used to form the outer sack include: polypropylene, polylactic acid materials, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, and ethylene-vinyl acetate copolymers in methylene chloride (Elvax 40).

These polymers are characterized as having the following (physical, mechanical, chemical, biomechanical) properties and ranges of properties: good tensile strength, low coefficient of elasticity, capacity for soft tissue in growth or replacement in vivo, binding affinity for BMP, TGF-Beta, and other bone, fibrous and cartilage tissue growth factors, resistance to fracture, and biocompatability. If the recipient's hair is used as the outer sack, such hair would be treated according to the following process. This process includes one or a combination of the following: Heparin SO4 treatment, dextran, protease, elastase, collagenase guanidine hydrochloride, and lithium bromide exposure. The hair would be woven or blended together using one of the following techniques. These techniques include: denaturation, acid treatment, loom and machine weaving.

After a portions or all of a dysfunctional disk is removed, the sack can be inserted in the inter-diskal space. The disk material can be removed using a number to techniques currently on the market. Thereafter, the sack can, by way of example only, be inserted through a cannula in a minimally invasive technique in order to position the sack in the space between two adjacent vertebral bodies. After this procedure is complete, the sack can be injected and filled with the appropriate polymer or other material. These materials can be state-dependant such that at one temperature, which is different than that of the body temperature of the patient, the materials flow more easily through a needle or cannula and at about body temperature the materials become more able to support the weight along the spinal column. Thus the materials can become more viscous and resilient once attaining the temperature of the body of the patient.

As described above, in this embodiment, the disk is comprised of a woven hair which is then filled with a polymer.

Figure 2:
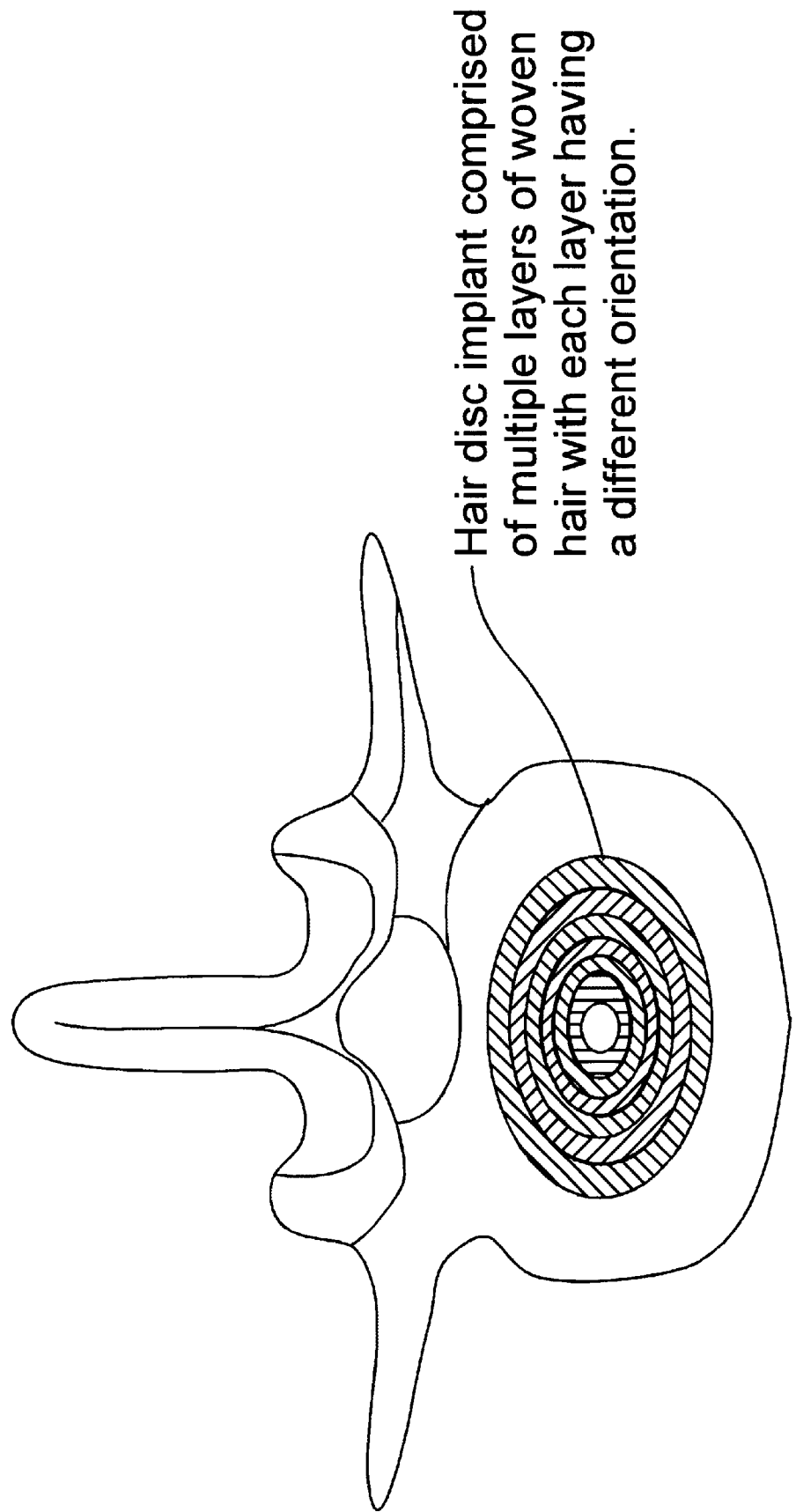
FIG. 2 is a representation of an embodiment of the second artificial disk structure of the invention with a disk comprised of hair with the hair in the center of the artificial disk specially treated to model the complex polymer found in a natural disk.

Second Artificial Disk Structure:

For this embodiment (FIG. 2), a disk replacement is made of processed hair entirely. The process for processing the hair is as follows. This process includes one or more of the following: the steps of denaturation, collagenase, protease, heparin sulphate, and dextran exposure. The hair can then be woven together in a mass and inserted into the disk space using a variety of techniques including from open surgery to insertion through an appropriately sized cannula. The hair can be a matrix structure characterized and described as follows. The matrix structure can include a denaturation, reduction of disulfide bonds (cyanogen bromide) proteolysis. Although not required for this embodiment, augmentation with cartilage producing Bone Morphogenic Protein (BMP) can allow a new intervertebral disk to form with the hair based collagen matrix as the cartilage inductive morphogenic substances and biomechanical stresses in the intervertebral space can induce differentiation of a new living intervertebral disk. Such Bone Morphogenic Protein can include the following types: BMP's 1–15, TGF-Beta, insulin-like growth factor, platelet derived growth factor. Additionally, the complex organic polymer which makes up much of the center of the normal disk and is responsible for its properties can be chemically created from hair and processed collagen to use as the central matrix of the artificial disk. A process for treating the hair based collagen matrix, in order to create the central nucleus of the artificial disk is as follows. This method includes one or more of the following steps of heparin sulphate or other polyanionic compound denaturation, and guanidine hydrochloride exposure. An outer woven hair bag would still be used in this case to confer the necessary biomechanical properties. This hair bag or sack can be constructed and have the properties of the sack previously described above. In the embodiment, the hair disk implant is comprised of multiple layers of woven hair with each layer having a different orientation.

The chemical processing of hair to modify its structure for use as (i) a Morphogenic protein carrier, and to (ii) increase its flexibility so it can be used as a strong "net" for use as a annulus replacement is as follows: This process includes mechanical weaving, partial denaturation, heparin treatment, collagenase and proteolytic treatment.

BMP (a cartilage and bone growth factor), in a particular embodiment can be carried by a product known as Poloxamer 407. The characteristics of this material are found in Table 1 below.

TABLE 1

Pluracare ® F 127 Prill
CTFA/INCI: Poloxamer 407

| Specifications | |
|---|---|
| Cloud Point (10% aqueous, ° C.) | ≧100 |
| Color (APHA) | ≦120 |
| Water Content (%) | ≦0.75 |
| pH (2.5% aqueous) | 6.0 to 7.4 |
| Description | Product Number |
| PluracareF 127 surfactant is a block copolymer of ethylene glycol and propylene glycols | 547427 |
| Appearance | |
| White solid in the form of small beads | |
| Solubility | |
| Water soluble | |
| Application | |
| Due to their low skin and eye irritation, the Pluracare grades find particular application in the cosmetic industry. Pluracare F 127 is used as a solubilizer and emulsifier in a wide variety of areas from cosmetics to oral care products. At concentrations of about 20% in water it forms stable, clear, ringing gels in which a wide variety of ingredients can be incorporated. It is also used as a solubilizer. Its HLB is in the range of 18 to 23. CAS Number: 9003-11-6 Molecular Weight: ~12,600 Manufacture: BASF Corporation, 3000 Continental Drive, North, Mount Olive, New Jersey 07826-1234 | |

A specific example of Poloxamer used as a BMP carrier is found in Table 2. Table 2 demonstrates a method that has successfully caused BMP to be injected into animal subjects and create cartilage and bone growth. Specific results of this example include formation of a mature ossicle of bone with bone marrow cells in middle of the injection site. The response was dose related.

TABLE 2

Poloxamer 407 as a Carrier for BMP
Materials & Method

| | |
|---|---|
| 1 | A 25 w/w % Poloxamer 407 was prepared by adding sterile water to it in a beaker at 3° Celsius temperature |
| 2 | Magnetic stirrer was used until Poloxamer had dissolved in the solute |

TABLE 2-continued

Poloxamer 407 as a Carrier for BMP
Materials & Method

| | |
|---|---|
| 3 | Aliquots of 1 cc was withdrawn in six syringes and poured in six vortex tubes |
| 4 | Two of each 2 mg, 5 mg, 10 mg hBMP (human native Bone Morphogenic Protein) samples were added to each vortex tube |
| 5 | The tubes were vortexed until the hBMP had distributed evenly in the solute |
| 6 | The contents of each vortex tube were injected in a mouse hindquarter muscle |
| 7 | The mice were sacrificed at 21 days and radiographic/histologic evaluations were performed |

From the above it can be appreciated that animal hair can be a carrier for BMP. Additionally Poloxamer 407 and similar compounds can be a carrier for BMP. Further Poloxamer 407 and similar compounds can be used as a BMP carrier in conjunction with the use of hair to make a artificial disk. The BMP in such an arrangement would create bone and cartilage on the outer periphery of the artificial disk in order to assist the artificial disk to bond with the upper and lower vertebral bodies which border the disk space. Additionally the BMP can assist the artificial disk to form an artificial nucleus.

Additionally in another embodiment of the invention Poloxamer 407 and like compounds can be used as a film, a gel, or a fluid in order to prevent post surgical adhesions. This material is prepared as follows in a preferred embodiment in order to be positioned adjacent to a surgical site and be effective an anti-adhesion material. The method for preparing this compound is as follows: 25% gel of Poloxamer 407 prepared by weighing 25 grams of poloxamer crystal in a beaker and adding distilled $H_2O$ in a cold room at less than 3° C. to bring the weight to 100 grams. Magnetic stirrer is used until a homogenous liquid is obtained. This will form a gel at room temperature.

Examples of BMP which can be used with the present invention can be obtained from a review of U.S. Pat. Nos. 4,563,489; 4,857,456; 4,795,804; all of which are incorporated herein by reference. Other examples for the promotion of bone growth can be found in the following U.S. Patents all of which are incorporated herein by reference: U.S. Pat. Nos. 5,531,791 and 5,484,601. Additionally polylactic acid can be used as a BMP carrier for the above disk replacement embodiments, as well as Gelfoam®, collagen, polyesther polymer mesh, composites of collagen and BMP, titanium fiber with BMP with or without non-collagenase proteins, polydioxanone, polyphosphazenes and BMP, ceramic collagen composite, expanded polytetrafluoroethylene barrier membranes, ethylene-vinyl acetate copolymers in methylene chloride (Elvax 40), composites of human fibrin, BMP/NCP in a polymethacrylate delivery system, sintered biodegradable b-tricalcium phosphate, composites of BMP and synthetic hydroxdyapatite mesh, hydroxy apatite adsorbed BMP, calcium sulphate, polylactic acid polymer composites, composites of poly-D (lactide coglycolide, and composites of e-caprolactone, high molecular weight polylactic acid homopolymers, composites of poly-2-hydroxyethyl methacrylate sponge, composites of polysulfone, polydioxanone, polyphosphazenes, cyanoacrylate, squalene, calcium glycerophosphoric acid, dextran, carbon, collagen type 1, and methyl pyrrolidinone.

Other features, aspects and objects of the invention can be obtained from a review of the figures.

It is to be understood that other embodiments of the invention can be developed and fall within the spirit and scope of the invention.

I claim:

1. A carrier for a morphogenic protein comprising human hair and a copolymer of ethylene glycol and propylene glycols.

2. The carrier of claim 1 for bone morphogenic protein.

3. The carrier for a morphogenic protein of claim 1 wherein the copolymer is a block copolymer of ethylene glycol and propylene glycols.

4. The carrier of claim 3 for bone morphogenic protein.

* * * * *